United States Patent [19]

Jones et al.

[11] 4,123,225

[45] Oct. 31, 1978

[54] COMBUSTIBLE GAS DETECTORS

[75] Inventors: Eric Jones, Chelmsford; Rodney P. Townsend, Harlington, both of England

[73] Assignee: English Electric Valve Company Limited, Chelmsford, England

[21] Appl. No.: 812,695

[22] Filed: Jul. 5, 1977

[30] Foreign Application Priority Data

Jul. 6, 1976 [GB] United Kingdom ............... 27961/76

[51] Int. Cl.$^2$ ................ B01J 23/40; B01J 23/58; G01N 27/16; G01N 31/12
[52] U.S. Cl. ........................................ 422/98; 338/34
[58] Field of Search ................... 23/254 E, 232 E; 338/34; 73/23

[56] References Cited

U.S. PATENT DOCUMENTS

| 3,166,901 | 1/1965 | Bliss | 23/232 R X |
|---|---|---|---|
| 3,644,795 | 2/1972 | Taguchi | 23/254 E UX |
| 3,883,307 | 5/1975 | Kim | 23/254 E |
| 3,955,268 | 5/1976 | Chou et al. | 23/232 E X |
| 3,959,764 | 5/1976 | Allman | 338/34 |
| 4,036,592 | 7/1977 | Brown et al. | 23/232 E |

FOREIGN PATENT DOCUMENTS 1,387,412 3/1975 United Kingdom ............... 23/254 E Primary Examiner—Robert M. Reese
Attorney, Agent, or Firm—Diller, Brown, Ramik & Wight

[57] ABSTRACT

The invention provides a combustible gas detector in which a heatable wire filament embedded in a pellet comprising oxidation catalyst material exhibits a change in resistance occasioned by the change in its temperature which occurs due to the oxidation of a combustible gas passing over it.

The pellet is provided with an outer layer of inert non-catalytic material which tends to prevent non-volatile residues from reaching catalytically active regions of the detector.

17 Claims, 1 Drawing Figure

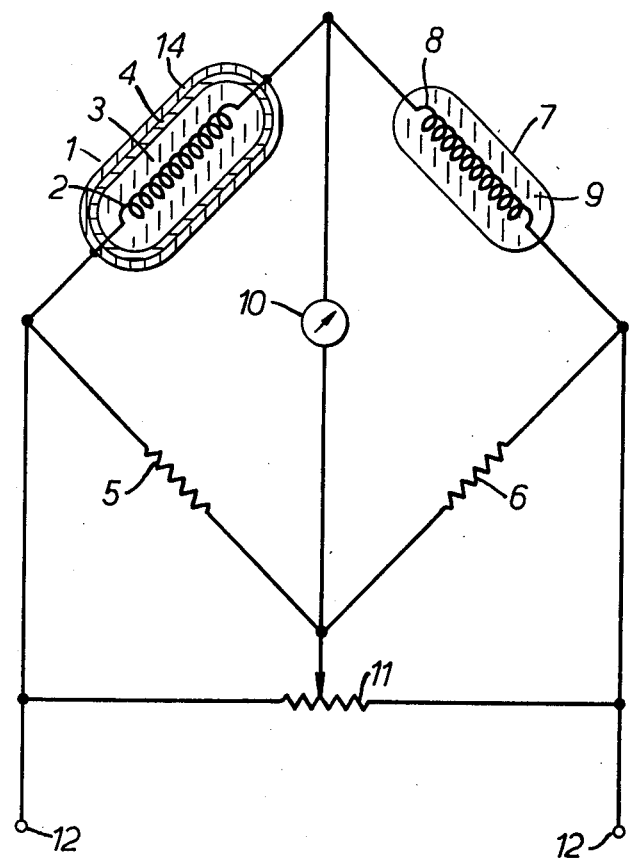

COMBUSTIBLE GAS DETECTORS

This invention relates to combustible gas detectors and more particularly to combustible gas detectors of the kind in which a heatable wire filament exhibits a change in resistance occasioned by the change in its temperature which occurs due to the oxidation of a combustible gas passing over it. Such gas detectors are usually included in a bridge circuit, the change in the balance of which as the resistance of the wire filament changes being utilised to provide an indication of the concentration of the combustible gas.

Whilst it is possible to use a naked wire filament it is also common to use a wire filament which is embedded in a pellet of ceramic material to provide a more rugged structure. It is also common to coat such a pellet with an oxidation catalyst which reduces the temperature at which oxidation of the combustible gas takes place, in order to reduce or prevent evaporaton of the wire filament so as to reduce any tendency for the characteristics of the gas detector to change in service.

A difficulty which has been experienced with gas detectors as described above is that in some circumstances changes in the electrical characteristics of the detectors occur in service. These changes are believed to be due to non-volatile residues deposited on the surface of the gas detector which tend to poison the catalyst and/or obstruct the normal flow of gas to the detector surface, so reducing the sensitivity of the device.

In the gas of burning leaded petroleum spirit vapour for example, solid lead tends to deposit on the surface of the detector which obstructs gas flow and/or tends to poison the catalyst.

The present invention seeks to provide an improved gas detector in which the above difficulty is mitigated.

According to this invention a gas detector comprising a heatable wire filament embedded in a pellet is provided with an outer layer of inert non-catalytic porous material tending to prevent non-volatile residues from reaching catalytically active regions of said detector.

The present invention is applicable generally to gas detectors of the embedded wire filament type, but preferably the gas detector is of the kind with which our United Kingdom Pat. No. 1,387,412 is concerned that is to say comprising a heatable wire filament embedded in a pellet consisting of a homogeneous mixture of an oxidation catalyst material and a substantially non-catalytic carrier material.

The invention is also applicable to gas detectors of the kind with which our co-pending U.K. Pat. application no. 25464/76 and corresponding U.S. Pat. application Ser. No. 732,861 now U.S. Pat. No. 4,072,467, are concerned that is to say comprising a heatable wire filament embedded in a pellet consisting of a homogeneous mixture of an oxidation catalyst material and a substantially non-catalytic carrier material, with a layer of oxidation catalyst material provided on the outside of said homogeneous pellet, in which case of course the outer layer of inert non-catalytic porous material is provided outside of the last mentioned layer of oxidation catalyst material.

Preferably said non-catalytic porous layer completely surrounds said pellet.

Preferably again said non-catalytic porous layer is of a material which is the same as a non-catalytic base carrier material used in the formation of the remainder of the pellet.

Preferably said porous material is alumina. Other examples of material which may be used to form said porous layer includes a zeolite or an alumina/zeolite mixture.

The invention is further described with reference to the accompanying drawing which illustrates schematically one gas detector bridge circuit including a gas detector in accordance with the present invention.

Referring to the drawing, 1 is a gas detector consisting of a heatable wire filament 2 of platinum embedded in a pellet 3 consisting of a homogeneous mixture of alumina and an oxidation catalyst material. In this example the oxidation catalyst material consists of palladium and platinum. Surrounding completely in this example, the pellet 3 is a layer 4 of oxidation catalyst material. In this example the oxidation catalyst material of the layer 4 is also a mixture of palladium and platinum formed by applying relatively high concentration solutions to the outside of the pellet 3. As so far described the gas detector is in accordance with the invention in our co-pending application no. 25464/76. In accordance with the present invention a layer 14 of alumina is provided on the layer 4 to completely surround the latter and the basic pellet 3.

The gas detector 1 is included in one arm of a balanced bridge arrangement consisting of resistors 5 and 6 of equal value and a compensating element 7. The compensating element 7 consists of a wire filament 8 of platinum embedded in a pellet 9 consisting of a homogeneous mixture of alumina, and a poison, potassium hydroxide, adapted to inhibit the oxidation of combustible gases. Across the bridge is connected a voltmeter 10, calibrated to indicate combustible gas concentrations. The meter 10 is arranged to be set to zero by the adjustment of the slider on a potentiometer 11. Terminals 12 are provided to be connected to a source of power providing both the heating current for the filaments 2 and 8 and voltage for the bridge.

Except for the nature of the gas detector 1, the arrangement is, in fact, as known per se.

In operation the gas detector 1 and compensating element 7 are exposed to normal atmosphere and the slider potentiometer 11, adjusted to give a zero reading on meter 10. The gas detector 1 and compensating element 7 are then exposed to the atmosphere which it is required to monitor. In the case of burning petroleum spirit vapour, lead oxidises and tends to remain on the surface of the porous layer 14 whilst the hydrocarbon content tends to diffuse through the porous layer 14 to the layer 4 to oxidise in the normal way. No oxidation occurs on the surface of compensating element 7. As previously the temperature of the filament 2 rises with a consequent change in its resistance. The reading of meter 10 then provides a measure of concentration of combustible gases in the atmosphere.

In the manufacture of the gas detector 1, the filament 2 is first wound and then cleaned. A solution of palladium chloride, platinum chloride, concentrated hydrochloric acid, distilled water and an aluminium nitrate solution is made up in the following quantities:

1 gram of palladium chloride
1 gram of platinum chloride
12.5 ml of concentrated hydrochloric acid
12.5 ml of distilled water
100 ml of saturated aluminum nitrate solution at 20° C.

A pellet (pellet 3) is then built up upon the platinum filament 2 by an evaporation technique as known per se.

A solution of palladium chloride, platinum chloride, concentrated hydrochloric acid, distilled water and an aluminum nitrate solution is then made up in the following quantities:

1 gram of palladium chloride
1 gram of platinum chloride
25 ml 2.5N hydrochloric acid
3 ml saturated aluminum nitrate solution at 20° C.

Using this solution a layer (layer 4) is then formed around the pellet previously formed, again by an evaporation technique.

An outer layer (layer 14) is then formed around the layer (layer 4) previously formed, again by an evaporation technique using a saturated aluminum nitrate solution.

The compensating element 7 is also formed by an evaporation technique.

As with known gas detector elements, prior to operation the element is "activated" by operating the element at elevated temperature in a reducing atmosphere.

Again in order to compensate for any differences in the surface colours of the detector element and compensatory element resulting in differences in their thermal emissivities leading to a change in the balance of the bridge, a compensating resistor (not shown) may be connected across the compensating element 7.

We claim:

1. A gas detector comprising a heatable wire filament embedded in a pellet and provided with an outer layer of non-catalytic porous material tending to prevent non-volatile residues from reaching catalytically active regions of said detector.

2. A detector as claimed in claim 1 and wherein said non-catalytic porous layer completely surrounds said pellet.

3. A detector as claimed in claim 1 and wherein said non-catalytic porous layer is of a material which is the same as a non-catalytic base carrier material used in the formation of the remainder of the pellet.

4. A detector as claimed in claim 1 and wherein said porous material is alumina.

5. A detector as claimed in claim 1 and wherein said non-catalytic porous layer comprises a zeolite material.

6. A detector as claimed in claim 1 and wherein said non-catalytic porous layer comprises an alumina/zeolite mixture.

7. A detector as claimed in claim 1 and wherein said pellet consists of a homogeneous mixture of an oxidation catalyst material and a substantially non-catalytic carrier material.

8. A detector as claimed in claim 7 and wherein a layer of oxidation catalyst material is provided on the outside of said pellet, said outer layer of non-catalytic porous material being provided on the outside of said last-mentioned layer of oxidation catalyst material.

9. A detector for a gas in the presence of non-volatile residue comprising, in combination:
a heatable wire filament having a resistive characteristic which varies with temperature;
catalytically active means surrounding said filament for altering the temperature of said filament in the presence of the gas to be detected; and
an outer layer of inert porous material on said catalytically active means, said inert porous material being non-catalytic and being evaporatively deposited onto said catalytically active means whereby to preserve the non-catalytic nature of the outer layer and prevent the reaction of non-volatile residue with said outer layer.

10. A detector as defined in claim 9 wherein said inert porous material is a zeolite.

11. A detector as defined in claim 9 wherein said inert porous material comprises a mixture of alumina and zeolite.

12. A detector as defined in claim 9 wherein said catalytically active means comprises a pellet within which said filament is embedded, said pellet consisting of a homogeneous mixture of an oxidation catalyst material and a substantially non-catalytic carrier material evaporatively deposited onto said filament.

13. A detector as defined in claim 12 wherein said inert porous material is a zeolite.

14. A detector as defined in claim 12 wherein said inert porous material comprises a mixture of alumina and zeolite.

15. A detector as defined in claim 12 wherein said catalytically active means also includes a layer of oxidation catalyst material evaporatively deposited onto said pellet.

16. A detector as defined in claim 15 wherein said inert porous material is a zeolite.

17. A detector as defined in claim 15 wherein said inert porous material comprises a mixture of alumina and zeolite.